US00PP28554P2

(12) United States Plant Patent
Lannes

(10) Patent No.: US PP28,554 P2
(45) Date of Patent: Oct. 24, 2017

(54) ***HIBISCUS* PLANT NAMED 'LANGILA'**

(50) Latin Name: *Hibiscus rosa-sinensis*
Varietal Denomination: Langila

(71) Applicant: Robert M. Lannes, Malause (FR)

(72) Inventor: Robert M. Lannes, Malause (FR)

(73) Assignee: D.H.M. INNOVATION, Malause (FR)

( * ) Notice: Subject to any disclaimer, the term of this patent is extended or adjusted under 35 U.S.C. 154(b) by 0 days.

(21) Appl. No.: 15/330,115

(22) Filed: Aug. 9, 2016

(51) Int. Cl.
*A01H 5/02* (2006.01)

(52) U.S. Cl.
USPC ..... Plt./257

(58) Field of Classification Search
USPC ..... Plt./257
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hibiscus* named 'Langila' that is characterized by its large uniform flowers that are yellow in color with pink centers, its floriferous bloom habit with flowers that stay open for 2 to 3 days, its early blooming and freely flowering habit, its vigorous growth habit, its upright, medium sized, uniform, well-branched and compact plant habit, and its foliage that is resistant to pathogens common to *hibiscus*, including *Pseudomonas* sp., *Phythium* sp., and *Phytophthora* sp.

2 Drawing Sheets

Botanical classification: *Hibiscus rosa-sinensis.*
Cultivar designation: 'Langila'.

BACKGROUND OF THE INVENTION

The present invention relates to a new and distinct cultivar of *Hibiscus rosa-sinensis* named 'Langila' and will be referred to hereafter by its cultivar name, 'Langila'. 'Langila' is a new cultivar of tropical *hibiscus* grown for use as a landscape and container plant.

The new cultivar was developed through an ongoing breeding program conducted by the Inventor in Malause, France. The objectives of the breeding program are to develop new cultivars of *Hibiscus* that exhibit large and brightly colored flowers, self-branching, high flower bud counts, and compact plant habits.

'Langila' arose from a cross made by the Inventor in July of 2009 between unnamed plants of *Hibiscus rosa-sinensis* from the breeding program, reference no. si 679-8 (not patented) as the female parent and reference no. si 6433-2 (not patented) as the male parent. 'Langila' was selected as a single unique plant from the resulting seedlings in September of 2013.

Asexual propagation of the new cultivar was first accomplished by stem cuttings in Malause, France in June of 2012 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics the new cultivar. These attributes in combination distinguish 'Langila' as a new and distinct cultivar of *Hibiscus.*

1. 'Langila' exhibits large uniform flowers that are yellow in color with pink centers.

2. 'Langila' exhibits a floriferous bloom habit with flowers that stay open for 2 to 3 days.
3. 'Langila' exhibits an early blooming and freely flowering habit.
4. 'Langila' exhibits a vigorous growth habit.
5. 'Langila' exhibits an upright, medium sized, uniform, well-branched and compact plant habit.
6. 'Langila' exhibits foliage that is resistant to pathogens common to *Hibiscus*, including *Pseudomonas* sp., *Phythium* sp., and *Phytophthora* sp.

The female parent of 'Langila' differs from 'Langila' in having flowers that are smaller in size and solid yellow in color and in having a lower flower bud count. The male parent of 'Langila' differs from 'Langila' in having much smaller flowers that are red in color and in having leaves that are lighter green in color. 'Langila' can be most closely compared to the *Hibiscus* cultivars 'Lemonade' (not patented) and 'President's Red' (not patented). 'Lemonade' is similar to 'Langila' in having flowers that are yellow with a pink eye in color and in having an upright well-branched plant habit. 'Lemonade' differs from 'Langila' in being less floriferous and in having flowers that are larger with a larger center that is not as true pink and petal margins that are more ruffled. 'President's Red' is similar to 'Langila' in having a floriferous blooming habit and similar foliage color. 'President's Red' differs from 'Langila' in having smaller flowers that are red in color and in having a less vigorous growth habit.

BRIEF DESCRIPTION OF THE DRAWINGS

The accompanying colored photographs illustrate the overall appearance and distinct characteristics of the new *Hibiscus*. The photographs were taken of 18 month-old plants of 'Langila' as grown in a two-gallon container.

The photograph in FIG. 1 provides a side-view of 'Langila' in bloom.

Figure 1:
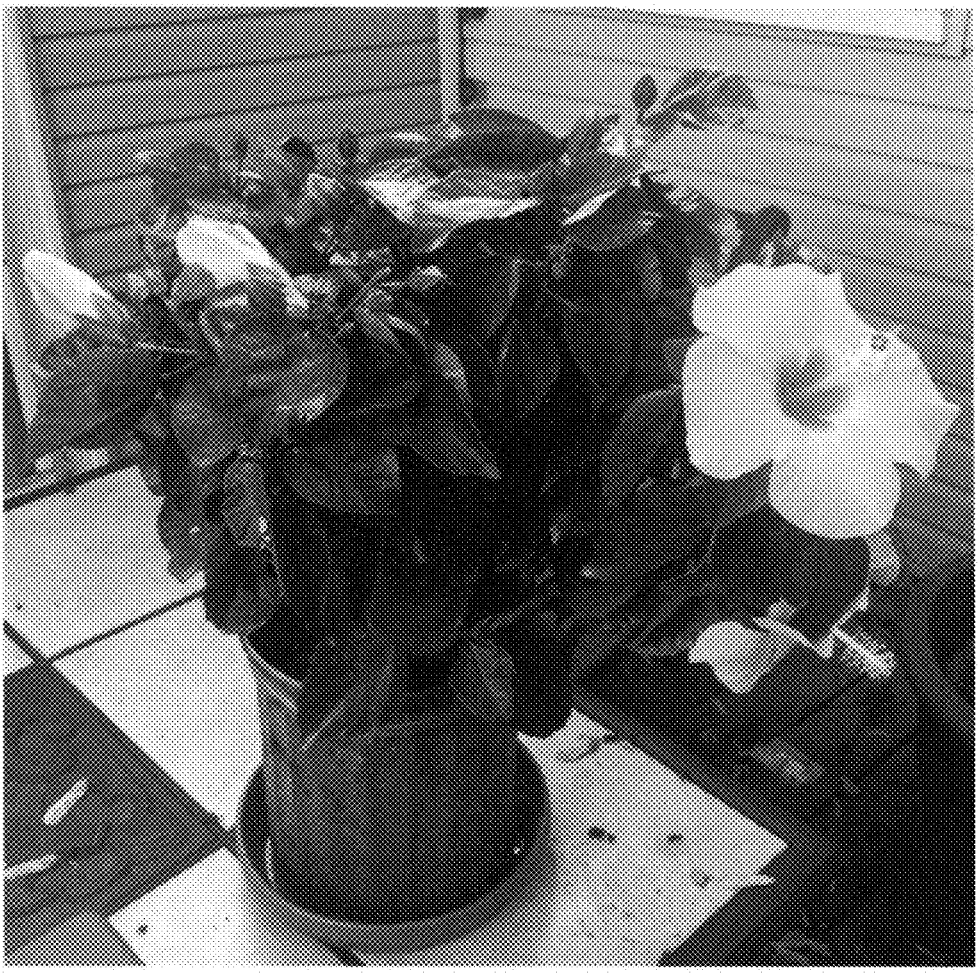
Figure 2:
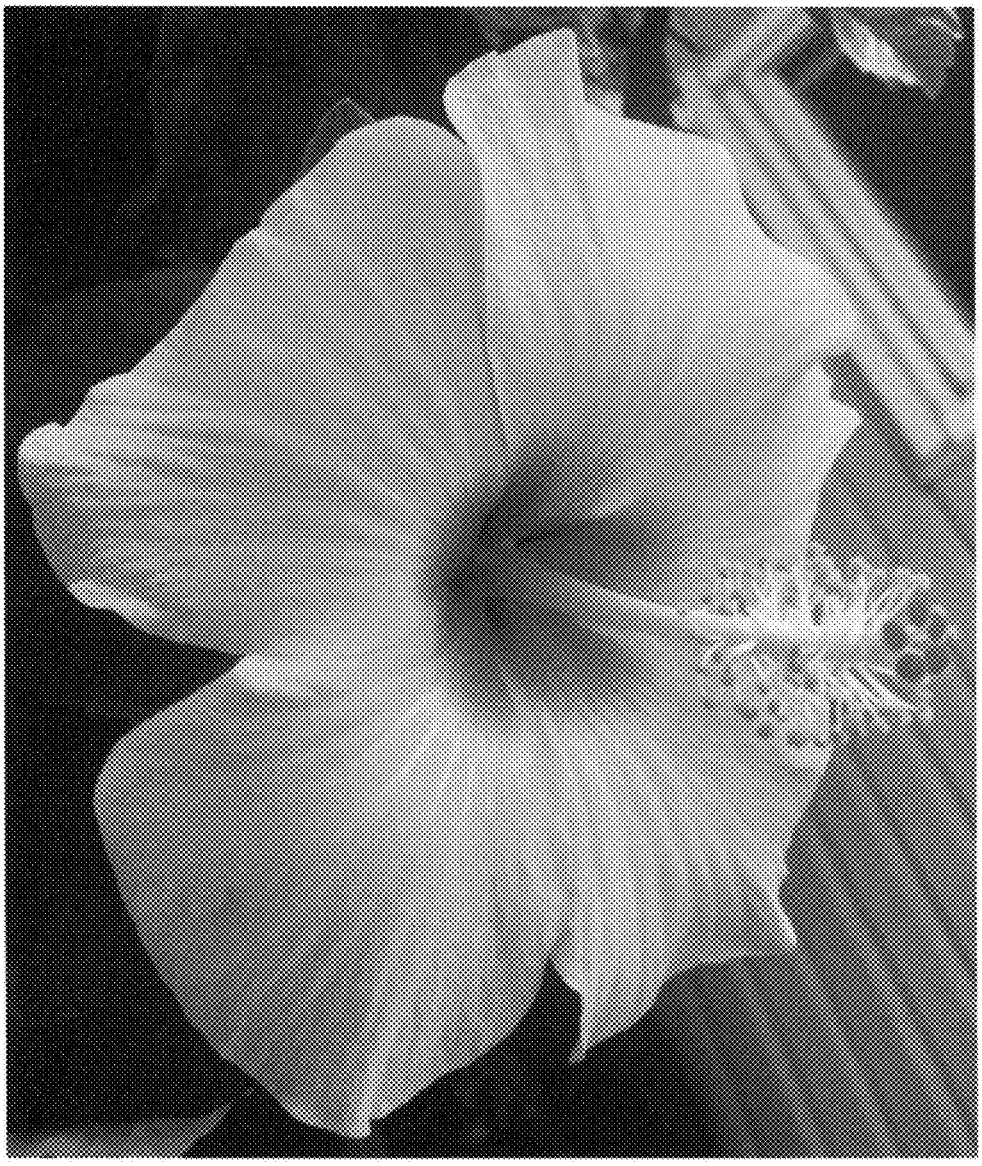

The photograph in FIG. 2 provides a close-up view of a flower of 'Langila'.

The colors in the photographs are as close as possible with the photographic and printing technology utilized and the color values cited in the Detailed Botanical Description accurately describe the colors of the new *Hibiscus*.

DETAILED BOTANICAL DESCRIPTION OF THE PLANT

The following is a detailed description of 18 month-old plants of the new cultivar as grown in two-gallon containers in a greenhouse in Grand Saline, Tex. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period.*—Continuously producing when grown in temperatures 55° F. to 90° F.

*Plant type.*—Tropical evergreen shrub.

*Plant habit.*—Upright, medium sized, uniform, well-branched and compact plant habit.

*Height and spread.*—An average of 32 cm in height and 52 cm in spread as grown in a two-gallon container and reaches an average of 2.7 m in height and 2.1 m in spread when mature in the landscape.

*Hardiness.*—Tropical; at least in U.S.D.A. Zones 9 to 10.

*Diseases.*—Resistance to pathogens common to *Hibiscus*, including *Pseudomonas, Phythium,* and *Phytophthora.*

*Root description.*—Fibrous roots, 161A in color.

*Propagation.*—Stem cuttings.

*Root development.*—Roots initiate in about 56 days and develop as a young plant in about 6 months.

*Growth rate.*—Vigorous.

Stem description:

*Shape.*—Rounded.

*Stem color.*—New growth; NN137B, mature wood; 197B and 199C.

*Stem size.*—Average of 30 cm in length, up to 1 cm in width.

*Stem surface.*—New growth; Glabrous, mature wood; woody, finely striated, bark-like.

*Stem aspect.*—Held in multiple angles, growing upright to slightly outward.

*Stem strength.*—Strong.

*Branching.*—Heavy branching habit, growing from the base, upright to outward.

*Internode.*—Average of 1 cm.

*Stipules.*—1 to 2 per leaf node, varying between linear to lanceolate to obovate in shape, an average of 1 cm in length and 5 mm in width, acute apex, truncate base, outer surface; 136A in color, glossy and leathery texture, inner surface; 137A in color, shiny and matte texture.

Foliage description:

*Leaf shape.*—Varying between ovate and deltoid.

*Leaf division.*—Simple.

*Leaf base.*—Rounded and truncate.

*Leaf apex.*—Acute.

*Leaf venation.*—Pinnate, veins match leaf color.

*Leaf margins.*—Serrate and wavy.

*Leaf attachment.*—Petiolate.

*Leaf arrangement.*—Alternate.

*Leaf orientation.*—Downward from petiole.

*Leaf aspect.*—Varying between, flat and slightly curled upward with wavy margins.

*Leaf surface.*—Upper surface glabrous, glossy with leathery texture, lower surface very finely puberulent with matte texture.

*Leaf color.*—Young and mature leaves upper surface NN137A, lower surface 146A.

*Leaf size.*—An average of 7.5 cm in length and 6 cm in width when mature.

*Leaf quantity.*—An average of 8 leaves per lateral stem, average of 15 cm in length.

*Petioles.*—An average of 2.5 cm in length and 2 mm in diameter, NN137B in color, surface is finely pubescent with a slight sheen overlay.

Flower description:

*Inflorescence type.*—Flowers are solitary from upper leaf axils.

*Lastingness of flowers.*—An average of 2 to 3 days, self cleaning.

*Flower size.*—An average of 9 cm in depth and 15.5 cm in diameter.

*Flower fragrance.*—Very slight pleasant fragrance.

*Flower shape.*—Rotate.

*Flower number.*—An average of 3, occasionally 4 flowers and buds present per stem at one time, continuously produces throughout the summer.

*Flower aspect.*—Outward when fully open to slightly pendulous.

*Flower bud.*—Elliptic in shape, an average of 8 cm in length and 2.5 cm in width (including calyx), color is 15A with sepal portion 144A, glabrous surface.

*Flower attachment.*—Peduncle.

*Petals.*—5, un-fused, slightly overlapping, oblanceolate in shape, an average of 7 cm in length and 6 cm in width, slightly serrate and wavy margins, rounded apex, base is cuneate slightly oblique and adnate to base of style slightly re-curved, lower surface is dull, upper surface is satiny and waxy near the base (throat), color of upper surface is 9A with veins in the mid-section NN155D and blending to 67A at the base (throat), color lower surface is 12A, mid-section to base is 4D and very slightly flushed with 63C.

*Calyx.*—Campanulate in shape, average of 3 cm in length and 2.5 cm in diameter.

*Epicalyx.*—Comprised of 6 bracts held upright surrounding sepals, lanceolate in shape, apiculate apex, truncate base, average of 1 cm in length and 5 mm in width, color of both surfaces is 144A, both surfaces are glabrous and dull.

*Sepals.*—5, base 40% fused, an average of 2 cm in length and 1.5 cm in width, color of both surfaces is 144A, outer surface is puberulent and inner surface is glossy, acute apex, truncate base.

*Peduncles.*—An average of 4 cm in length and 3 mm in diameter, strong, average angle upright to outward, 144A, glabrous and glossy surface.

*Pedicels.*—Not present, flowers are solitary from terminal leaf axils.

*Receptacle.*—7 mm in diameter, 144B in color, glabrous and glossy surface.

Reproductive organs:

*Gynoecium.*—1 pistil, stigmas; 5, round in shape, 2 mm in diameter, fur-like surface and N45B in color on style arms; 3 mm in length, 19A in color, surface is pubescent and slightly glossy, style; average of 7.5 cm in length, very glossy surface, 11B flushed with 67A, ovary; oblong in shape with pointed apex, 1.5 cm in length and 7 mm in width, 10B in color.

*Androecium.*—Stamens; average of 70, stamens are clustered and implanted into upper portion of style, anthers; dorsifixed and orbicular in shape, 2 mm in diameter, and 21B in color; filament; 6 mm in length and 11D in color, pollen; abundant in quantity and 21B in color.

*Fruit/seeds.*—None observed to date.

It is claimed:

1. A new and distinct cultivar of *Hibiscus* plant named 'Langila' as herein illustrated and described.

* * * * *